US005607856A

United States Patent [19]

Moon et al.

[11] Patent Number: 5,607,856
[45] Date of Patent: Mar. 4, 1997

[54] SOIL TREATMENT FOR AGRICULTURE

[75] Inventors: Darin J. Moon, Burley, Id.; Anne J. Anderson, Providence, Utah

[73] Assignee: High Desert Research Group, Inc., Burley, Id.

[21] Appl. No.: 160,503

[22] Filed: Dec. 1, 1993

[51] Int. Cl.$^6$ .................. C12N 1/06; C12N 1/04
[52] U.S. Cl. .................. 435/259; 422/28; 422/32; 436/8
[58] Field of Search .................. 435/259; 422/28, 422/32; 436/8

[56] References Cited

U.S. PATENT DOCUMENTS

| | | | |
|---|---|---|---|
| 3,893,943 | 7/1975 | Willard, Sr. | 252/428 |
| 4,103,001 | 7/1978 | Schather | 424/660 |
| 4,917,815 | 4/1990 | Beilfuss et al. | 252/186.23 |

FOREIGN PATENT DOCUMENTS

| | | |
|---|---|---|
| 3-290388 | 12/1991 | Japan . |
| 2057417 | 4/1981 | United Kingdom . |

OTHER PUBLICATIONS

Ilan Chet, Biological Control of Soil–borne Plant Pathogens with Fungal Antagonists in Combination with Soil Treatments, in *Biological Control of Soil–Borne Plant Pathogens*, pp. 15, 18–23, ed.: Hornby, D., (1990).

Simic, Michael G., D. S. Bergtold and L. R. Karam, Generation of oxy radicals in biosystems, Mutation Research, 214:3–12, (1989).

Kemira Biotech, Mycostop Biofungicide Today, in *Plant Growth–Promoting Rhizobacteria Newsletter*, No.10:3, column 1, (1993).

VandeMark et al. *The Microbes*. 1987. pp. 442–443.

*Primary Examiner*—Michael G. Wityshyn
*Assistant Examiner*—Blaine Lankford
*Attorney, Agent, or Firm*—Townsend and Townsend and Crew LLP

[57] ABSTRACT

This invention provides for compositions and methods for sterilizing soil using oxygen radicals. The soil is treated with an aqueous solution of an activated oxygen species after pretreatment with a water soluble phenolic complex including a divalent cation having redox potential, a cation redox reducing agent. The combination of the activated oxygen species and water soluble phenolic complex is sufficient to reduce soil microorganisms by at least 40% without leaving an accumulative toxic residue.

47 Claims, No Drawings

SOIL TREATMENT FOR AGRICULTURE

FIELD OF THE INVENTION

This invention relates to methods for sterilizing soil using activated oxygen species.

BACKGROUND OF THE INVENTION

In agriculture, there are many pathogens that will reduce both productivity and quality of crops. Enormous losses result each year due to the infestations of plant pathogens. One of the most difficult areas of pathogen control is in soil-born organisms. Products that give the desired levels of control are often toxic to the plant as well. In addition, these products are often extremely toxic to the environment, and are being banned from production and use. Therefore, the idea of a product or products that can accomplish desired levels of control without the toxicity would indeed be valuable.

One of the greatest problems created in agriculture today is the use of toxic chemicals as a means of pathogenic control. In the chemical boom of the 1950's, 1960's and 1970's, many chemicals were created as a means of controlling organisms that caused plant damage. Unfortunately, at the same time, little or no advances were being made to understand the complexities involved in a biological system, and these chemicals were applied to the soil or plant with only the control or elimination of the pathogen in mind. It was not appreciated that by eliminating the pathogen, many beneficial organisms were eliminated as well. This is significant in that when the organism presented itself at a later date, the pathogen met little or no resistance due to the fact that all of its "competitors" had been eliminated. Now an even larger problem is at hand. The only means of control available to the farmer now is the use of more of the same chemical for control. This too has its problems in that as in all biological systems, evolution or adaptation is a fact of life. Now resistance is present which means that new and more toxic chemicals must be used, and now the farmer is caught in a endless cycle of depending on toxic chemicals.

SUMMARY OF THE INVENTION

This invention provides for methods of sterilizing soil by generating oxygenated radicals. The method comprises contacting soil with an aqueous solution of an activated oxygen species, a divalent cation having redox potential, a cation redox reducing agent and a water soluble phenolic complex, wherein the amount of solution contacting with soil is effective to reduce soil microorganisms by at least 40%. Preferred activated oxygen species are hydrogen peroxide, peracetic acid, sodium peroxide, potassium peroxide, calcium peroxide, potassium oxide and magnesium peroxide. Preferred divalent cation are $Mn^{++}$, $Fe^{++}$, $Cu^{++}$ and $Zn^{++}$. Preferred cation redox reducing agents are ascorbate, dithiothreitol, and dithioerythritol. The water soluble phenolic complex is preferably extracted from humic material, sea weed extract, fish extract or manure. The oxygen radicals include hydroxyl radicals, peroxy radicals, phenoxy radicals and superoxide anions.

The method preferably involves acidifying the water soluble phenolic complex generally with a organic acid such as acetic acid or citric acid to a pH of between about 6.5 to 3.0 and more preferably between about 4.0 to 3.0.

The target microorganisms are nematodes, fungi and bacteria. After sterilization, one can optionally add non-plant pathogenic microorganisms to the soil to both repopulate and prevent pathogenic microorganisms from rapidly repopulating the soil. Preferred microorganisms include such species as Pseudomonas, Streptomyces, Bacilli, Mycorrhizae Trichoderma, and Gliocladium.

A preferred mode of application is first saturating the soil with an aqueous solution comprising the divalent cation, the cation redox reducing agent and the water soluble phenolic complex; draining the soil to field capacity and then saturating the soil with an aqueous solution comprising the activated oxygen species. The phenolic complex is preferably acidified with acetic acid.

In addition to the above methods there are compositions provided by this invention. Such compositions include a combination of an aqueous solution of an activated oxygen species, a divalent cation having redox potential, a cation redox reducing agent and water soluble phenolic complex in an amount to effectively reduce microorganism population in soil by at least 40%. The preferred components are as stated for the methods.

This invention further relates to the pretreatment of the soil with an aqueous solution comprising a divalent cation having redox potential, a cation redox reducing agent and a water soluble phenolic complex. The preferred ratio of a divalent cation to reducing agent to phenolic complex is about 60 to 0.6 parts divalent cation: 60 to 0.6 parts reducing agent: 1 part phenolic complex. More preferably 30 to 0.3 parts divalent cation: 30 to 0.3 parts reducing agent: 1 part phenolic complex and most preferably about 10 to 0.1 parts divalent cation: 10 to 0.1 parts reducing agent: 1 part phenolic complex. The preferred components are as stated above for the methods. The preferred amount of water soluble phenolic complex has a final concentration of between 0.1–3% by weight to volume and most preferably about 1.0%.

Finally, these methods and compositions can also be used to sterilize containers such as soil conveying containers or vehicles. The invention can also be used to sterilize seeds and other plant parts such as food crops.

DEFINITIONS

The phrase "activated oxygen species" describes oxygenated compounds which serve as a source of oxygenated radicals. These compounds include hydrogen peroxide $H_2O_2$, hydroperoxides (ROOH), peroxides (ROOR), phenols (R$\phi$OH) or hydroxylated aromatics (ArOOH) where R is an alkane, alkene or alkyne, branched or unbranched, and of between 1 and 12 carbons and Ar is an aromatic ring usually of 6 carbons or a combination of such rings.

The phrase "cation redox reducing agent" is any reducing agent that donates electrons to a cation that has participated in the generation of an oxygenated radical. In certain instances, the cation is oxidized back to its active species thus acting as a "free radical pump", capable of again generating oxygenated radical species.

The phrase "divalent cation having redox potential" is any cation that participates as an electron donor in the reduction of the source of activated oxygen species.

The phrase "field capacity" refers to the percent water remaining in soil two or three days after having been saturated and after free drainage has practically ceased.

The phrase "oxygenated radicals" describes species of radicals generated by the reduction of oxygen, hydrogen peroxide ($H_2O_2$), hydroperoxides (ROOH), peroxides (ROOR), phenols, R$\phi$OH or hydroxylated aromatics (ArOOH). The one electron reduction of oxygen leads to formation of superoxide radical, as for example, superoxide anion ($\cdot O_2^-$). The reduction of hydrogen peroxide generates hydroxy radical ($\cdot OH$). The reduction of hydroperoxides or peroxides generate alkoxy radicals (RO$\cdot$). The reduction of phenols and R$\phi$OH generate phenoxy radicals (R$\phi$O$\cdot$). The reduction of hydroxylated aromatics generates aroxy radicals (ArO$\cdot$).

The phrase "soil saturation" is a conditions where all the pores in the soil are filled with water.

The term "water soluble phenolic complex" describes inactive phenolic residues which serve as a source of oxygenated radicals that are aromatic in nature, i.e., phenols, R$\phi$OH, and hydroxylated aromatics, that are water soluble. The water soluble phenolic complexes are extracted from various natural sources.

It is important that the water soluble phenolic complex remain water soluble in an acid environment as the generation of activated oxygen species are optimal below pH 7. In this regard, the invention provides extraction methods that produce a greater amount of phenolic complex that is water soluble at acid pHs than previous methods that used bases such as KOH. When mixed with KOH, the resulting chemical reaction breaks free many of the phenolic acids that makeup the phenolic complex and allows them to stay in suspension as long as the pH remains above 7.5. Below pH 7.0, the phenolic acid precipitate out of solution. The method of the invention entails the use of a catalyst previously disclosed in U.S. Pat. No. 3,893,943 titled "Novel Catalyst and Process for Preparing the Same", incorporated herein by reference. By reacting a material that contains phenolic acids with this catalyst, the resulting aqueous suspension of phenolic complex remains in solution below pH 7.0.

DETAILED DESCRIPTION

In the present invention, soil is sterilized by contacting the soil with an activated peroxide/phenolic [AP/P] solution. The AP/P solution comprises a variety of antimicrobial activated oxygen radicals. They are generated in the soil by reacting an activated oxygen species with a water soluble phenolic complex in the presence of a divalent cation having a redox potential and a cation redox reducing agent. The AP/P solution will sterilize soil without leaving an accumulative toxic residue.

A. Manufacturing the Activated Peroxide/Phenolic Solution

The AP/P solution comprises multiple components which can be present in a range of non-critical concentrations. The phenolic component is a water soluble phenolic complex. The water soluble phenolic complex is extracted from a variety of natural sources. It is preferred that the water soluble phenolic complex is acid stable, but it is not necessary. The invention will work using a crude mixture of humic acid or manure extract. These extracts may be obtained by leaching out soluble phenolics under alkaline conditions. The solution is then rendered acidic and filtered. The common sources of water soluble phenolics include peat, peat moss, coal, lignite, manure, seaweed and other natural plant sources. The preferred commercial source is called Leonardite and is available from American Colloid Co. 1500 West Shure Dr., Arlington Heights, Ill. Where appropriate the phenolics can be broken down into a powder or a fiber to facilitate extraction of the water soluble phenolic complex.

The soluble phenolics are preferably extracted by a Willard catalyst for carbonaceous extraction and modification. Willard catalysts allow for the extraction of soluble phenolics in basic solution without undesirable precipitation. These catalysts are known in the art and are described in U.S. Pat. No. 3,893,943 ['943]. They are available from a variety of commercial sources. A suitable Willard catalyst is High Tech Humics produced by Ag Concepts Corporation, 9350 Bienapfl, Boise Id., USA or RL33 produced by International Ag Labs, P.O. Box 788 Fairmont, Min. It is sold as a liquid and is manufactured by Ag Concepts according to example 1 of the '943 patent.

The extraction procedure is a two step process. The phenolic source is added to distilled water. The phenolic is generally a solid and is added to the water in a range of about 0.01–0.1 parts phenolic to 1 part water by weight. The liquid catalyst is then added to the solution in a range of 0.01 to 0.25 gallons of catalyst to 1 gallons of phenolic/water mix. Preferably the rate is between 0.05 to 0.15 gallons of catalyst to 1 gallon to phenolic/water mix. The pH of the solution is about 8.5.

The mixture of catalyst and phenolic source is allowed to react under agitation for between 6 and 48 hours. To increase the alkalinity of the solution, soda ash (anhydrous sodium carbonate) and ammonia are added to the mixture. The soda ash is added to a final concentration range of $1 \times 10^{-3}$ to $0.5 \times 10^{-2}$ by weight to 1 part water by weight. Commercial ammonia is available in a 21.5% solution and this standard ammonia liquid is added to the mixture at a rate of between $1 \times 10^{-3}$ to $0.5 \times 10^{-2}$ parts to one part water by liquid volumes. Preferably the ammonia liquid is added to the mixture at a rate of between $1.0 \times 10^{-3}$ to $0.2 \times 10^{-2}$ parts to one part water by liquid volumes.

The mixture is then allowed to react under agitation for between 6 and 36 hours. The insoluble phenolics in the mixture are allowed to settle to the bottom of the reaction vessel. Filtration or centrifugation can be used to shorten this time period.

The resulting solution is the water soluble phenolic complex. This complex has non-activated phenolic residues from which phenoxy radicals are generated. It is a stable, dark, black solution comprising between about 1 to 5%, optimally about 3% soluble phenolics. Acid soluble phenolics can be measured by standard means. For example the California Department of Food and Agriculture from the Feed & Fertilizer Section; Chemical Laboratory Services 3292 Meadowview Road; Sacramento, Calif. (Method #HA4/JC). Briefly, humic acids are dissolved by treatment with 1N sodium hydroxide and then precipitated with hydrochloric acid. The California method may be used for determining the percent acid insoluble humic acid in any given sample where the solid or liquid samples containing 0.5% or more humic acid and is provided in detail in Example 1 below.

Those of skill will understand that the above steps may be modified and optimized for different the phenolic sources to achieve yields of between 1 and 5%. For example while Leonardite is a standard commercial source of phenolics, the other listed sources can be used but the time of agitation and amounts of catalysts may need to be adjusted to provide suitable yields. Routine titration experiments, well within the skill of those in the art, can be used to optimize conditions according to the selection of phenolics.

Prior to use, the water soluble phenolic complex is combined with a divalent cation having redox potential and a cation redox reducing agent to yield the water soluble phenolic mixture. The ratio of redox reducing agent to divalent cation parts to acid parts to phenolic parts is 60–0.6: 60–0.6: 2.5–0.025: 1 and preferably about 10–1.0: 10–1.0: 1.0–0.1: 1. The divalent cation is typically a nontoxic salt of manganese, ferrous iron, copper or zinc. The molar concentration of the divalent cation is between about 0.1M to 1.0M. Manganese sulfate is a preferred salt at 0.17M. The cation redox reducing agent is a reducing agent and is preferably an organic molecule such as ascorbate, mercaptans, dithiothreitol and dithioerythritol. The preferred reducing agent is ascorbic acid. The reducing agent is added to a final molar concentration of between about 0.1M to 1.0M and is preferred at 0.16M. Optionally and preferably, the pH of the solution is adjusted to between 3 and 5 to acidify the solution. Suitable acids include acetic acid, citric acid, hydrochloric acid, sulfuric acid, as well as other acids which leave no toxic residue. The resulting soluble phenolic complex is then ready for use with activated oxygen species to create the soil sterilent.

B. Activated Oxygen Species

The soluble phenolic mixture is used in combination with an activated oxygen species to produce oxygen radicals that are the sterilizing agents of this invention. The activated oxygen species include but are not limited to hydrogen peroxide, peracetic acid and corresponding nontoxic salts, various salts of peroxides such as sodium peroxide, potassium peroxide magnesium peroxide or calcium peroxide and potassium oxide.

The activated oxygen species is diluted in water at a concentration range of between 1.0% and 0.01% by weight/volume if a salt and by volume/volume if as in hydrogen peroxide the oxygen generating species is soluble and available as a standard concentration in water. Preferably the activated oxygen species is present in the water at a concentration of about 0.1%–0.5%.

For example, hydrogen peroxide is available commercially in aqueous solutions of either 50% or 35%. The 35% solution is preferred. The 35% peroxide is diluted in water between about 35 to 3500 times and more preferably between about 70 and 350 times.

C. Sterilizing Soil with an AP/P Solution

Because the reaction of the activated oxygen species with the soluble phenolic mixture is immediate, the solutions must be kept separate and are preferably applied separately. The soluble phenolic mixture is typically added to the soil as a pretreatment and the activated oxygen species is added afterwards from within hours to a week. The preferred dilution rate is between 300 and 3,000 times. The soil or field is flooded with the water soluble phenolic complex to a depth of between 1 and 3 feet. The soil is allowed to drain to field capacity and the activated oxygen species is added.

The concentration of water soluble phenolic complex in contact with the soil is between $1.0 \times 10^{-3}\%$ and $0.5 \times 10^{-5}\%$ by weight to volume, and preferably $1 \times 10^{-4}\%$. The concentration of divalent cation in contact with the soil is between $10^{-5}$M and $10^{-7}$M, and preferably $10^{-6}$M. The concentration of the cation redox reducing agent in contact with the soil is between about $1 \times 10^{-5}$M and $1 \times 10^{-7}$M, and preferably about $10^{-6}$M.

The activated oxygen species concentration in contact with the soil is between about 0.01% and 1.0% by volume, and preferably of a concentration of 0.1–0.5% by volume. These amounts in combination with the water soluble phenolic complex are effective in causing a substantial reduction in soil microorganisms, preferably by 40% when assayed within one week.

The AP/P solutions can be used to treat soil prior to commercial sale. The solutions can also be used to treat fields prior to planting. Finally the solutions can be used to treat plantings and orchards where the solution is in direct contact with living roots.

Once the soil is treated, it is desirable to reconstitute the microflora with beneficial bacteria and fungi. These organisms may act as a antagonists to phytopathogenic species and may act as beneficial agents to promote plant growth. Suitable and beneficial organisms include Mycorrhizae, Bacilli, Pseudomonas, Streptomyces, Trichoderma, Tallaromyces, Gliocladium and species of yeast. Commercial inoculums are available and include Amaze™ and Arouse™ from International Ag Labs.

D. Sterilizing Seeds and Other Materials

In addition to sterilizing soil, the compositions described herein can be used as sterilizing agents for seeds and other surfaces both biological and man-made (containers or vehicles) without modification. In general, the exposure times can be shortened by a half or more. Routine titration experiments will provide optimum concentrations and exposure times. Such parameters will vary in accordance with the hardiness of the seed and the relative sensitivity of the microorganism being treated.

EXAMPLES

The following examples are provided by way of illustration only and not by way of limitation. Those of skill will readily recognize a variety of noncritical parameters which could be changed or modified to yield essentially similar results.

Example 1

Preparation of Phenolic Complex From Leonardite

A catalyst is used to extract the phenolic complex, in the form of humic acid, from Leonardite. Preparation of the catalyst is described in now expired U.S. Pat. No. 3,93,943, titled; Novel Catalyst and Process for Preparing the Same, issued Jul. 8, 1975, incorporated herein by reference. Briefly, anhydrous calcium chloride in an amount of 0.66 gram and magnesium sulfate heptahydrate in an amount of 1.32 grams are dissolved in 2 liters of deionized water with stirring and warming until solution is complete. Then 95 grams of sodium silicate pentahydrate having a molecular ratio of sodium oxide to silicon dioxide of 1:1 is added to the solution with stirring and continued warming to produce a white suspension of finely divided particles of the reaction product. Most of the reaction product will appear in the form of a colloidal suspension.

After setting for 10 minutes, the suspension of the reaction product is heated to 80° C. and 201 grams of sulfated castor oil is added with stirring. The average molecular weight of the sulfated castor oil is 400 and contains 50% of water. The turbidity will lessen somewhat as the suspension is heated at 80°–90° C. for 1 hour with vigorous stirring to produce catalyst micelles. The concentrated aqueous suspension of catalyst micelles thus prepared will have a viscosity similar to that of water. In addition, the catalyst can be obtained commercially under the product name "High Tech Humics" produced by Ag Concepts Corporation of 9350 Bienapfl, Boise, Id., USA.

To extract the humic acid from Leonardite, one adds to 9 gallons of distilled water, 1 gallon of catalyst, 2.5 pounds of Leonardite (American Colloid Co. 1500 West Shure Dr. Arlington Heights, Ill., USA). The composition is allowed to agitate for 24 hours at room temperature. Four ounces of soda ash (Sigma Chemical Co., St. Louis, Mo., USA) and 2 ounces of 21.5% ammonia (Sigma Chem Labs). The complete mixture is agitated for another 24 hours and allowed to settle without agitation for 48 hours. During this time the larger non-soluble particles sink to the bottom of the tank. The upper portion of the tank contains the soluble humic acid and is removed from the tank. The solution is a dark black.

This procedure will yield a solution of about 3.0% humic acid. The amount of humic acid is measured by the following procedure:

The precise method follows:

EQUIPMENT AND REAGENTS 1) centrifuge
2) 100 ml screw cap centrifuge bottles
3) 1N NaOH
4) 1% NaOH (10 g/liter)
5) conc. HCl
6) 100° C. drying oven
7) mechanical shaker

ANALYSIS

1) Weigh appropriate size sample into a 100 ml wide mouth screw top bottle to give close to 0.2 g of dry humic acid ppt.
2) Add 50 mls 1N NaOH. seal tightly.
3) Shake on mechanical shaker for 1.5 hours for solids, 30 min for liquids.
4) Rinse the cap with 5 mls. 1% NaOH to recover phenolics adhering to the cap.
5) Centrifuge for 25 minutes at 2000 rpm.
6) Decant supernatant liquid into a second weighed bottle.
7) Add 10 ml 1% NaOH to first bottle, shake vigorously, centrifuge again.
8) Add the supernatant liquid to the second centrifuge bottle.
9) To the combined extracts in the second bottle add conc. HCl until the pH is adjusted to between 1 and 2.
10) Centrifuge the sample for 25 minutes at 2000 rpm.
11) Carefully decant the liquid and discard.
12) Add 25 mls distilled water (previously adjusted to pH 1–2 with HCl) to the bottle with ppt. shake vigorously to free all ppt. from bottom and centrifuge again.
13) Again, carefully decant the liquid and discard.
14) Repeat line 12 two more times.
15) Dry the bottle with humic acid overnight at 100°–110° C.
16) Cool in desiccator and weigh.

The following formula is used to calculate % humic acid in a given sample:

$$\% \text{ Humic acid} = \frac{\text{Wt. dried residue}}{\text{Sample Wt.}} \times 100$$

Example 2

Preparation of Phenolic Complex From Lignite

In a manner similar to Example 1, the catalyst can be used to extract the phenolic complex from lignite.

Example 3

Preparation of water soluble Phenolic Mixture

To one gallon of 3.0% humic acid based solution prepared in Example 1, add 2 gallons of distilled water, 1 pound ascorbic acid, (Sigma Chem. Labs) 1 pound manganese sulfate, (Sigma Chem Labs) and 1 gallon of 5% acetic acid. This mixture is now ready for use in the soil sterilizing method of the invention.

Example 4

Method of Sterilizing Soil

The soil is pre-irrigated to provide a saturated soil water content to a depth of 1 to 3 feet, meaning the soil profile can no longer hold water. The soil is next drained for one day to field capacity to allow air spaces to form to accommodate subsequent applications of the water soluble phenolic complex. At the end of this one day period, four gallons of the water soluble phenolic mixture prepared in Example 3 is added into a controlled drip irrigation system watering one acre. The system has a flow of 450 gallons per acre per hour and is allowed to flow for 4 hours using one half gallon/hour emitters equally dispersed over the one acre. The soil is allowed to drain for 24 hours and is then flooded again with a 0.1% final concentration of hydrogen peroxide in water. The hydrogen peroxide solution is applied using the same drip irrigation system described above. Six gallons of 35% hydrogen peroxide is injected into the system watering one acre with 450 gallons of water per hour over a four hour period.

This results in a soil saturated with a 0.1–0.5% hydrogen peroxide solution. This is achieved over a 4–8 hour period to allow for effective soil penetration.

A 72 hour period is allowed for the pesticide reaction to take place and also to allow any unreacted $H_2O_2$ to dissipate from the soil. At the end of the 72 hour period, the soil can be inoculated with beneficial bacteria and/or fungi. In addition, antibiotics, or fungicides can be added.

Example 5

Post Sterilization Soil Amendments

Because the treatment leaves no toxic residues, pathogenic and nonpathogenic microorganisms will begin competing shortly after treatment. To prolong the benefits of the treatment a commercial inoculum, Arouse™, is added to the soil at a rate of 1 pound per acre according to the manufacturer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for sterilizing soil by generating oxygenated radicals said method comprising contacting soil with an aqueous solution of an activated oxygen species, a divalent cation, a cation redox reducing agent and a water soluble phenolic complex which is extracted from a material selected from the group consisting of humic material, plant material, animal material and manure, wherein the amount of solution contacting with soil is effective to reduce soil microorganisms and nematodes by at least 40%.

2. The method of claim 1 wherein said activated oxygen species is selected from the group consisting of hydrogen peroxide, peracetic acid, sodium peroxide, potassium peroxide, calcium peroxide, potassium oxide and magnesium peroxide.

3. The method of claim 2 where the activated oxygen species is peracetic acid.

4. The method of claim 1 where the activated oxygen species is hydrogen peroxide in a concentration between about 1.0 and 0.01% by volume.

5. The method of claim 4 wherein said hydrogen peroxide is at a concentration of between about 0.1 and 0.5% by volume.

6. The method of claim 1 wherein said divalent cation has a concentration between $10^{-5}$M and $10^{-7}$M.

7. The method of claim 1 wherein said divalent cation is selected from the group consisting of $Mn^{++}$, $Fe^{++}$, $Cu^{++}$ and $Zn^{++}$.

8. The method of claim 7 wherein said divalent cation is $Mn^{++}$.

9. The method of claim 1 wherein said cation redox reducing agent is selected from the group consisting of ascorbate, dithiothreitol, and dithioerythritol.

10. The method of claim 9 wherein said cation redox reducing agent has a concentration of between $1.0 \times 10^{-5}$M and $1.0 \times 10^{-7}$M.

11. The method of claim 1 wherein said water soluble phenolic complex has a concentration of between about $1.0 \times 10^{-3}$ to $1.0 \times 10^{-5}$% weight/volume.

12. The method of claim 11 wherein said water soluble phenolic complex has a concentration of $1.0 \times 10^{-4}$% by weight/volume.

13. The method of claim 1 wherein said activated oxygen species is selected from the group consisting of hydroxyl radicals, peroxy radicals, phenoxy radicals and superoxide anions.

14. The method of claim 1 wherein said water soluble phenolic complex is acidified with an organic acid selected from the group consisting of acetic acid and citric acid.

15. The method of claim 14 wherein said organic acid is acetic acid.

16. The method of claim 1 wherein said solution has a pH of between about pH 6.5 and pH 3.0.

17. The method of claim 1 wherein said solution has a pH of between about pH 4.0 and pH 3.0.

18. The method of claim 1 wherein said microorganisms are fungi and bacteria.

19. The method of claim 1 comprising the further step of adding non-plant pathogenic microorganisms to the soil after sterilization.

20. The method of claim 19 wherein said non-plant pathogenic microorganisms are selected from the group consisting of Pseudomonas, Streptomyces, Bacilli, Mycorrhizae, Trichoderma, and Gliocladium.

21. The method of claim 1 further comprising: (a) saturating the soil with an aqueous solution comprising the divalent cation, the cation redox reducing agent and the water soluble phenolic complex; (b) draining the soil to field capacity and (c) saturating the soil with an aqueous solution comprising the activated oxygen species.

22. A composition for sterilizing soil consisting of: an acidic aqueous solution of an activated oxygen species, a divalent cation having redox potential, a cation redox reducing agent and water soluble phenolic complex which is extracted from a material selected from the group consisting of humic material, plant material, animal material and manure.

23. The composition of claim 22 wherein said activated oxygen species is selected from the group consisting of hydrogen peroxide, peracetic acid, sodium peroxide, potassium peroxide, calcium peroxide, potassium oxide and magnesium peroxide.

24. The composition of claim 23 where the activated oxygen species is hydrogen peroxide.

25. The composition of claim 22 wherein said activated oxygen species is hydrogen peroxide in a concentration between 0.01% and 1.0% by volume/volume.

26. The composition of claim 25 wherein said hydrogen peroxide is of a concentration of between about 0.1% and 0.5% by volume/volume.

27. The composition of claim 22 wherein said divalent cation has a concentration between $10^{-5}$M and $10^{-7}$M.

28. The composition of claim 22 wherein said divalent cation is selected from the group consisting of $Mn^{++}$, $Fe^{++}$, $Cu^{++}$ and $Zn^{++}$.

29. The composition of claim 22 wherein said divalent cation is $Mn^{++}$.

30. The composition of claim 22 wherein said cation redox reducing agent is selected from the group consisting of ascorbate, dithiothreitol, or dithioerythritol.

31. The composition of claim 22 wherein said water soluble phenolic complex has a final concentration of between about $1.0 \times 10^{-3}$ to $0.5 \times 10^{-5}$% by weight to volume.

32. The composition of claim 31 wherein said water soluble phenolic complex has a final concentration of about $1.0 \times 10^{-4}$% by weight to volume.

33. The composition of claim 22 wherein said activated oxygen species is selected from the group consisting of: hydroxyl radicals, peroxy radicals, phenoxy radicals and superoxide anions.

34. The composition of claim 22 wherein said water soluble phenolic complex is acidified with an organic acid selected from the group consisting of acetic acid and citric acid.

35. The composition of claim 34 wherein said organic acid is acetic acid.

36. The composition of claim 34 wherein said water soluble phenolic complex has a pH of between about pH 6.5 and pH 3.0.

37. The composition of claim 22 wherein said water soluble phenolic complex has a pH of between about pH 4.0 and pH 3.0.

38. An aqueous solution for pretreating soil for sterilization comprising a divalent cation having redox potential, a cation redox reducing agent and a water soluble phenolic complex which is extracted from a material selected from the group consisting of humic material, plant material, animal material and manure.

39. The solution of claim 38 wherein the ratio of divalent cation to reducing agent to phenolic complex is about 60 to 0.6 parts divalent cation: 60 to 0.6 parts reducing agent: 1 part phenolic complex.

40. The solution of claim 38 wherein the ratio of divalent cation to reducing agent to phenolic complex is about 10 to 1.0 parts divalent cation: 10 to 1.0 parts reducing agent: 1 part phenolic complex.

41. The solution of claim 38 wherein said divalent cation has a concentration between about 0.1M and 1.0M.

42. The solution of claim 38 wherein said divalent cation is selected from the group consisting of $Mn^{++}$, $Fe^{++}$, $Cu^{++}$ and $Zn^{++}$.

43. The solution of claim 42 wherein said divalent cation is $Mn^{++}$.

44. The solution of claim 38 wherein said cation redox reducing agent is selected from the group consisting of ascorbate, dithiothreitol, or dithioerythritol.

45. The solution of claim 38 wherein said water soluble phenolic complex has a final concentration of between 0.1–3% by weight to volume.

46. The solution of claim 38 wherein said water soluble phenolic complex has a final concentration of 1.0% by weight/volume.

47. A method of sterilizing a surface harboring microorganisms, said method comprising contacting the surface with an aqueous solution of an activated oxygen species, a divalent cation, a cation redox reducing agent and a water-soluble phenolic complex which is extracted from a material selected from the group consisting of humic material, plant material, animal material and manure.

* * * * *